(12) United States Patent
Goshayeshgar et al.

(10) Patent No.: US 9,216,057 B2
(45) Date of Patent: Dec. 22, 2015

(54) STEERABLE CATHETER SYSTEM AND METHOD OF USING A STEERABLE CATHETER SYSTEM TO DISSECT AND EVACUATE TISSUE

(71) Applicant: KYPHON SARL, Neuchatel (CH)

(72) Inventors: Mojan Goshayeshgar, Atherton, CA (US); Michael A. Smith, San Jose, CA (US)

(73) Assignee: Kyphon SARL, Neuchatel (CH)

( * ) Notice: Subject to any disclaimer, the term of this patent is extended or adjusted under 35 U.S.C. 154(b) by 315 days.

(21) Appl. No.: 13/840,010

(22) Filed: Mar. 15, 2013

(65) Prior Publication Data

US 2014/0276745 A1    Sep. 18, 2014

(51) Int. Cl.
*A61B 18/18*    (2006.01)
*A61B 18/14*    (2006.01)
*A61B 19/00*    (2006.01)
*A61B 17/00*    (2006.01)
*A61B 18/00*    (2006.01)

(52) U.S. Cl.
CPC ......... *A61B 18/1492* (2013.01); *A61B 19/5212* (2013.01); *A61B 2017/00318* (2013.01); *A61B 2018/00601* (2013.01); *A61B 2018/144* (2013.01)

(58) Field of Classification Search
CPC ............... A61B 2018/1412; A61B 2018/1452; A61B 2018/1492; A61B 18/1492; A61B 19/5212; A61B 2017/00318; A61B 2018/00601
USPC .......................................... 606/45, 39, 40, 49
See application file for complete search history.

(56) References Cited

U.S. PATENT DOCUMENTS

| 5,722,975 | A | 3/1998 | Edwards et al. | |
|---|---|---|---|---|
| 6,551,302 | B1 | 4/2003 | Rosinko et al. | |
| 6,585,717 | B1 | 7/2003 | Wittenberger et al. | |
| 8,052,704 | B2 | 11/2011 | Olson | |
| 2003/0023239 | A1* | 1/2003 | Burbank et al. | 606/45 |
| 2010/0174283 | A1* | 7/2010 | McNall et al. | 606/45 |
| 2012/0004595 | A1* | 1/2012 | Dubois et al. | 604/22 |

FOREIGN PATENT DOCUMENTS

WO        9846149 A1    10/1998

* cited by examiner

*Primary Examiner* — Theodore Stigell
*Assistant Examiner* — Michael Carey

(57) ABSTRACT

A steerable catheter system is provided including an elongated shaft having a proximal end, a distal end and an outer surface. The outer surface includes at least one cavity configured to facilitate movement of the distal end relative to the proximal end so as to steer the elongated shaft. A catheter tip is attached to the distal end of the shaft. The catheter tip comprises a curved body having at least one RF cutting edge and at least one non-cutting area recessed from the at least one cutting edge.

22 Claims, 5 Drawing Sheets

STEERABLE CATHETER SYSTEM AND METHOD OF USING A STEERABLE CATHETER SYSTEM TO DISSECT AND EVACUATE TISSUE

TECHNICAL FIELD

The present disclosure generally relates to medical devices, and more particularly to a surgical system and method employing a steerable catheter device to dissect and evacuate tissue.

BACKGROUND

One of the most common causes of low back pain for the middle-aged and elderly population is lumbar spinal stenosis (LSS), LSS is a medical condition in which the spinal canal narrows and compresses the spinal cord and nerves at the level of the lumbar vertebra. Namely, LSS involves the narrowing of the lower spinal canal and subsequent entrapment of the cauda equina roots by hypertrophy of the osseous and/or soft tissue structures surrounding the lumbar spinal canal. This is usually due to the common occurrence of spinal degeneration that occurs with aging.

LSS is often associated with incapacitating pain in the back and lower extremities, difficulty ambulating, leg paresthesias and weakness. The typical symptom is increased pain in the legs with walking (pseudoclaudication), which can markedly diminish one's activity level. The characteristic syndrome associated with lumbar stenosis is termed neurogenic intermittent claudication.

There are a number of surgical procedures for the treatment of LSS, including lumbar laminectomy and open decompression surgery. Lumbar laminectomy is designed to remove a small portion of the bone over the nerve root and/or disc material from under the nerve root to give the nerve root more space. Laminotomy is a microdecompression procedure in which a part of the lamina is removed to relieve pressure, or to allow access for the surgeon to be able to remove the offending portion of the disc or the bone spur.

From a surgical perspective, minimally invasive techniques are preferable when possible. To this end, the use of catheters is desirable, which can be introduced into body cavities and manipulated to surgically remove certain tissues. Numerous catheters have been designed to perform various surgical functions. However, many challengers exist, particularly for spinal surgical procedures. For example, it is difficult to fit and maneuver catheters within the geometry of the interspinous space and make accurate cuts therein. This could significantly increase the risk of unintentional injury to adjacent areas. This disclosure provides improvements over these prior art technologies.

SUMMARY

In one embodiment, in accordance with the principles of the present disclosure, a catheter system is provided. The catheter system includes an elongated shaft having a proximal end, a distal end and an outer surface. The outer surface includes at least one cavity configured to facilitate movement of the distal end relative to the proximal end so as to steer the elongated shaft. A catheter tip is attached to the distal end of the shaft. The catheter tip comprises a curved body having at least one radio frequency (RF) cutting edge and at least one non-cutting area recessed from the at least one cutting edge.

In one embodiment, the catheter system includes an elongated shaft having a proximal end, a distal end, an inner surface and an outer surface. The outer surface includes at least one cavity configured to facilitate movement of the distal end relative to the proximal end so as to steer the elongated shaft. The inner surface defines a passageway. A catheter tip is attached to the distal end of the shaft. The catheter tip comprises a curved body having at least one radio frequency (RF) cutting edge and at least one non-cutting area recessed from the at least one RF cutting edge. At least one electrode is disposed on the cutting edge configured to emit a cutting radio frequency signal. A radio frequency generator is operably connected to the catheter tip to provide radio frequency energy to the at least one electrode. A vacuum is attached to the proximal end of the shaft so as to provide suction to clear cut tissue from the passageway.

In one embodiment, a method of treating a hypertrophied ligamentum flavum in a patient using a steerable catheter device is provided. The method includes the steps of: providing a catheter system comprising: an elongated shaft having a proximal end, a distal end, an inner surface and an outer surface, wherein the outer surface includes at least one cavity configured to facilitate movement of the distal end relative to the proximal end so as to steer the elongated shaft, wherein the inner surface defines a passageway, a catheter tip attached to the distal end of the shaft, wherein the catheter tip comprises a curved body having at least one radio frequency (RF) cutting edge and at least one non-cutting area recessed from the at least one RF cutting edge, at least one electrode disposed on the at least one cutting edge configured to emit a cutting radio frequency signal, a radio frequency generator operably connected to the catheter tip to provide radio frequency energy to the at least one electrode, and a vacuum attached to the proximal end of the shaft so as to provide suction to clear cut tissue from the passageway; steering the shaft through tissue such that the catheter tip is positioned adjacent the hypertrophied ligamentum flavum; and activating the radio frequency generator to cut tissue. The catheter design may also incorporate a flexible camera to enable direct visualization and hence more accurate cut.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

Like reference numerals indicate similar parts throughout the figures.

DETAILED DESCRIPTION

Figure 1:
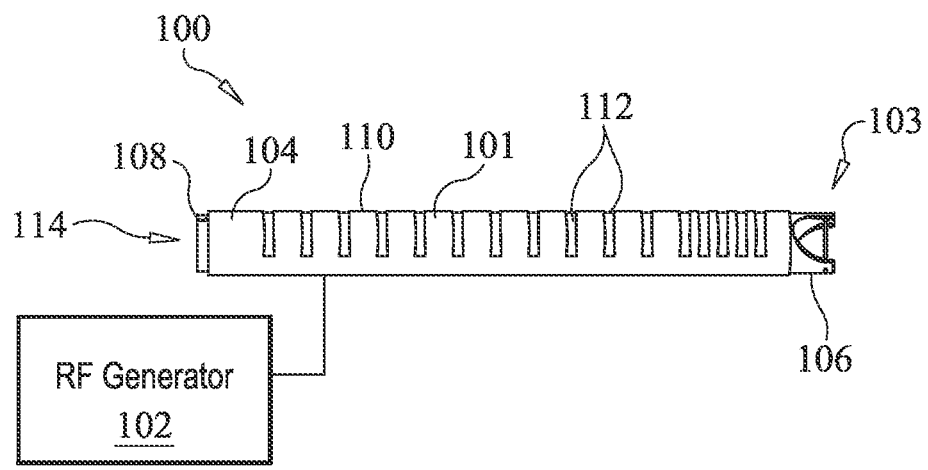
FIG. 1 is a side view of a catheter system in accordance with the principles of the present disclosure.

The exemplary embodiments of the surgical system and related methods of use disclosed are discussed in terms of medical devices for the treatment of musculoskeletal disorders and more particularly, in terms of a surgical system 100 and method for nerve destruction.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided.

In one embodiment, the catheter is a steerable/deflectable catheter with active steering or single plane deflection capability. The reach of the catheter is designed to dissect along the ligamentum flavum. The catheter may also have built in irrigation/suction lumens. The tip is designed to cut through the ligamentum flavum while protecting the dura from mechanical or thermal collateral damages. The cutting tip uses pulsed radio frequency (RF) to generate a plasma-mediated discharge along the exposed edge of an insulated tip, creating an effective cutting edge while minimizing collateral thermal damage. Access through the interspinous space with or without distraction allows for bilateral access to the ligamentum flavum through one incision and one access cannula. A flexible camera can be incorporated into the catheter design to allow for direct visualization of space.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, catheters that are preformed to have different sizes and shapes.

It is envisioned that the present disclosure may be employed to treat spinal disorders, such as, for example, stenosis. It should be understood that the present principles are applicable to any spinal disorder or disorders and defects in other areas of the body. It is contemplated that the present disclosure may be associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 100 can be fabricated from biologically acceptable materials suitable for medical applications, including metals, synthetic polymers, ceramics and bone material and/or their composites, depending on the particular application and/or preference of a medical practitioner. For example, the components of system 100, individually or collectively, can be fabricated from materials such as stainless steel alloys, commercially pure titanium, titanium alloys, Grade 5 titanium, super-elastic titanium alloys, cobaltchrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference.

The components of system 100, individually or collectively, may also be fabricated from a heterogeneous material such as a combination of two or more of the above-described materials. The components of system 100 may be monolithically formed, integrally connected or include fastening elements and/or instruments, as described herein.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there are illustrated components of system 100 in accordance with the principles of the present disclosure.

It is noted that, as used in this specification and the appended claims, the singular forms "a," "an," and "the," include plural referents unless expressly and unequivocally limited to one referent. Thus, for example, reference to "a covering" includes one, two, three or more coverings.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there are illustrated components of system 100 in accordance with the principles of the present disclosure.

Figure 2:
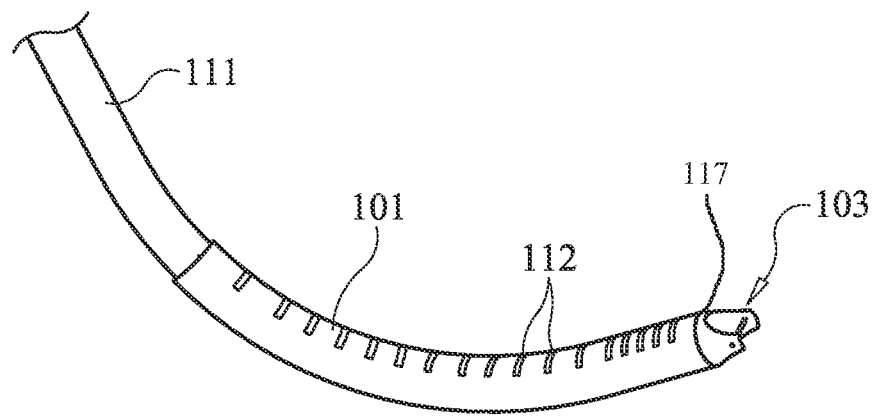
FIG. 2 is a perspective view of the system shown in FIG. 1.

System 100 includes an elongated shaft 101 of any shape, size or configuration adapted to fit in or at a desired surgical site. Shaft 101 includes a proximal end 104, a distal end 106, an inner surface 108 and an outer surface 110. Inner surface 108 defines a passageway 114. Shaft 101 has a linear configuration, as shown in FIG. 1. An inner member 111 is positioned within passageway 114. Inner member 111 comprises an elastic material, such as, for example, a super elastic metal, such as, for example, Nitinol. Inner member 111 is preformed to have an arcuate configuration, as shown in FIG. 2. In some embodiments, inner member 111 has a tubular configuration. That is, inner member 111 may include an inner surface that defines a passageway configured for disposal of instruments, such as, for example, a suction means and/or an irrigation means.

Outer surface 110 includes at least one cavity 112 extending perpendicular to an axis defined by shaft 101 through inner surface 108 and outer surface 110. Shaft 101 may include one or a plurality of cavities 112. In some embodiments, cavities 112 are provided in a linear arrangement such that cavities 112 are all aligned. In some embodiments, cavities 112 are uniformly spaced apart from one another. In some embodiments, cavities 112 are spaced apart more closely at distal end 106 than at proximal end 104. That is, the spacing between cavities 112 increases gradually from distal end 106 to proximal end 104, as shown in FIGS. 1 and 2, for example. This configuration allows a greater degree of bending at proximal end 104 than at distal end 106. It is envisioned that this configuration may be reversed. That is, the spacing between cavities 112 can increase gradually from proximal end 104 to distal end 106, to allow a greater degree of bending at proximal end 104 than at distal end 106.

Cavities 112 have a slot-like configuration such that each cavity 112 does not extend circumferentially about outer surface 110. That is, each cavity 112 extends through a first section of outer surface 110 without extending through an opposite second section of outer surface 110, the first and second sections defining a circumference of outer surface 110. It is envisioned that cavities 112 may be disposed at alternate orientations relative to the axis defined by shaft 101, such as, for example, transverse and/or other angular orientations such as acute or obtuse and/or may be offset or staggered and/or may be disposed at alternative angular orientations relative to the axis defined by shaft 101, depending on the requirements of a particular application.

Cavities 112 are configured to facilitate movement, such as, for example, bending of distal end 106 relative to proximal end 104 so as to allow a medical practitioner to deflect and steer shaft 101 to a desired position after shaft 101 is deployed from a surgical instrument, such as, for example a cannula. Shaft 101 may be delivered to a surgical site, such as, for example, a location adjacent a ligamentum flavum of a patient by delivering shaft 101 through a surgical instrument, such as, for example, a cannula having an inner surface defining a passageway having a uniform diameter along the length of the passageway of the cannula. Inner member 111 is disposed within passageway 114. When shaft 101 is disposed within the passageway of the cannula, inner member 111 deforms such that inner member 111 and shaft 101 each have a linear configuration. When shaft 101 extends through the cannula such that shaft 101 is spaced apart (positioned outside of) the passageway of the cannula, inner member 111 returns to its arcuate configuration. Because inner member 111 is disposed within passageway 114, as inner member 111 bends to return to its arcuate configuration, shaft 101 also bends such that shaft 101 also assumes an arcuate configuration. The bending of shaft 101 to impart an arcuate configuration to shaft 101 is facilitated by cavities 112. Therefore, cavities 112 allow inner member 111 and shaft 101 to move from a first orientation in which inner member 111 and shaft 101 are positioned within a cannula and have a linear configuration to a second orientation in which inner member 111 and shaft 101 are positioned outside a cannula and have an arcuate configuration. The amount of curvature of shaft 101 when shaft 101 is in the second orientation may be altered by modifying the number and location of cavities 112 to achieve the desired amount of curvature, according to the preference of a medical practitioner.

Shaft 101 may comprise a flexible, long, hollow tube which is capable of optionally passing materials such as guide wires, control wires, drugs, sensors, sensor fibers or wires, power, suction tubes, irrigation tubes, ultrasonic signals, drive shafts, etc. Materials such as guide wires, control wires, drugs, sensors, sensor fibers or wires, power, suction tubes, irrigation tubes, ultrasonic signals, drive shafts, etc. may also be passed through the passageway defined by the inner surface of inner member 111 when inner member 111 is positioned within passageway 114. It is envisioned that all or only a portion of shaft 101, cavities 112 and/or passageway 114 may have alternate cross section configurations, such as, for example, circular, oval, oblong, triangular, square, rectangular, polygonal, irregular, uniform, non-uniform, offset, staggered, undulating, arcuate, variable and/or tapered, according to the requirements of a particular application.

Distal end 106 of the shaft 101 includes at least one catheter tip 103. In some embodiments, catheter tip 103 includes a cylindrical distal portion 117 disposed in passageway 114 such that an outer surface of distal portion 117 engages inner surface 108 of shaft 101 to fix catheter tip 103 to shaft 101. It is envisioned that the outer surface of distal portion 117 and inner surface 108 of shaft 101 may each be threaded such that the threads on the outer surface of distal portion 117 engage the threads on inner surface 108 of shaft 101 to fix catheter tip 103 with shaft 101. It is further envisioned that distal portion 117 of catheter tip 103 may be disposed with shaft 101 in alternate fixation configurations, such as, for example, friction fit, pressure fit, locking protrusion/recess, locking keyway and/or adhesive. In some embodiments, a proximal end surface of distal portion 111 engages a distal end surface of shaft 101 to fix catheter tip 103 with shaft 101. In some embodiments, shaft 101 and catheter tip 103 are integrally formed or monolithic.

Catheter tip 103 includes at least one electrode to provide catheter tip 103 with at least one cutting edge, such as, for example, a radio frequency (RF) emitting edge. It is envisioned that catheter tip 103 may include one or a plurality of cutting edges. In some embodiments, system 100 includes a radio frequency (RF) generator 102 that delivers RF energy to the RF emitting cutting edge(s) and includes a power source (not shown). It is envisioned that generator 102 may be configured to deliver monopolar RF energy and/or bipolar RF energy or pulsed plasma RF energy.

Figure 7:
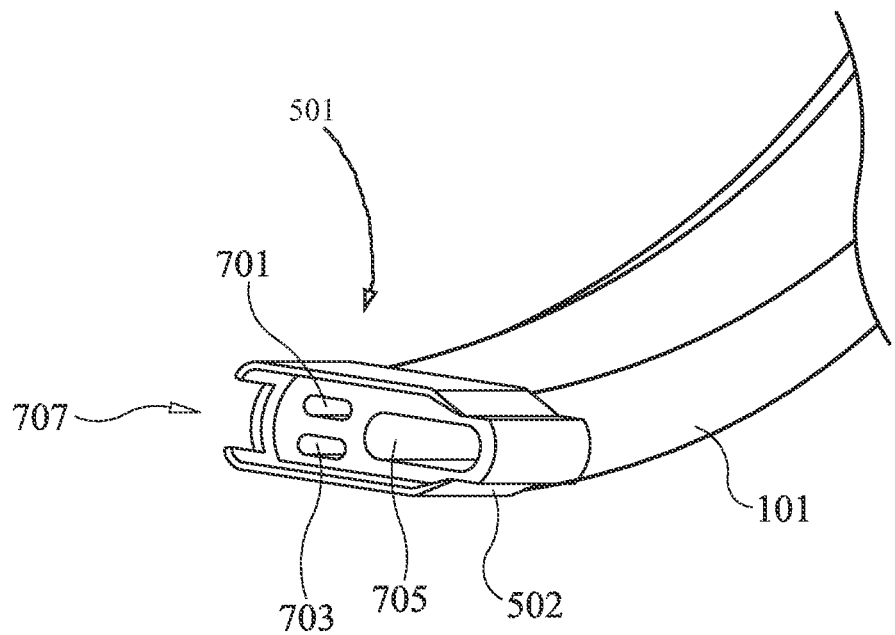
FIG. 7 is an enlarged, perspective view of components of the system shown in FIG. 5.

In some embodiments, shaft 101 may be configured to deflect in a single plane. This can be achieved by arranging cavities 112 in a linear arrangement on only one side of shaft 101, as shown in FIG. 1. Configuring shaft 101 to deflect in a single plane can also be achieved by providing shaft 101 with a non-round configuration such as a flattened, oblong shape having, e.g., a substantially rectangular cross-section (e.g., as shown in FIG. 7). This enables the shaft 101 to be positioned and moved to achieve various angles and curves which are substantially co-planar. For example, FIG. 2 depicts a side view of system 100 with shaft 101 in a deflected position (in the second orientation). It is envisioned that shaft 101 may be configured to deflect through multiple planes by providing a first series of cavities 112 arranged in a linear configuration on one side of shaft 101 and a second series of cavities 112 arranged in a linear configuration on an opposite side of shaft 101, the sides of shaft 101 defining the circumference of shaft 101. Inner member 111 is positioned within passageway 114 such that shaft 101 deflects through a first plane when shaft 101 is in the second orientation. Inner member 111 may be then be rotated 180 degrees within passageway 114 such that shaft 101 deflects through a second plane when shaft 101 is in the second orientation, the second plane being different than the first plane.

In some embodiments, catheter tips are provided which are designed to effectively cut through the ligamentum flavum while protecting tissues such as the dura against mechanical and/or thermal collateral damage, and which can access the interspinous space with or without distraction to allow for bilateral access to the ligamentum flavum through one incision and one access cannula (shaft 101). These objectives can be achieved through various configurations, as depicted and described herein.

Figure 3:
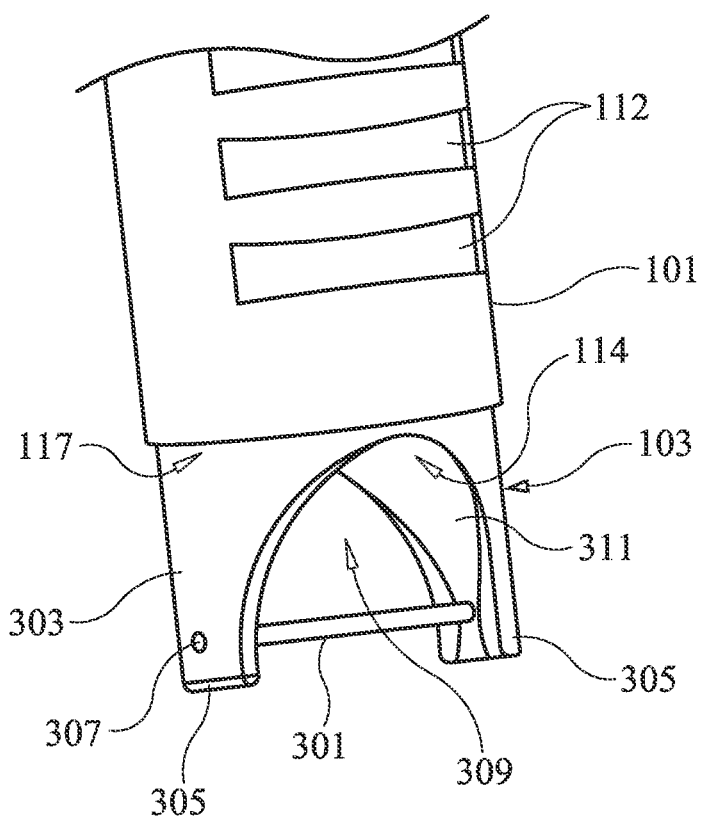
FIG. 3 is an enlarged, perspective view of a component of the system shown in FIG. 1.

FIG. 3 depicts an enlarged perspective view of catheter tip 103. Catheter tip 103 is in communication with passageway 114 such that cut tissue can be directed proximally from catheter tip 103 into passageway 114 for removal from a surgical site. In some embodiments, catheter tip 103 comprises a curved body 303 having two ends 305 defining a C-shaped recess 309. Body 303 may include a first area (a cutting area) configured for cutting e.g., tissue/bone, and a second area configured to be a non-cutting area, which may comprise, e.g., an insulating material, such as, for example, thermal plastic, to protect tissue/bone from mechanical or thermal damage or cutting action. Ends 305 are configured to prevent damage to adjacent tissue and/or nerves during dissection of the ligamentum flavum.

In some embodiments, the first area comprises a cutting edge in the form of a cutting wire 301 which may be affixed to each of the two ends 305, e.g., by being inserted into apertures 307 therein. Any alternate means for attaching cutting wire 301 to catheter tip 103 may be contemplated. Any of the cutting areas/edges described herein, including cutting wire 301, may comprise of any material which can effectively use RF energy to generate a plasma-mediated discharge and thus form an effective cutting edge, such as for example, platinum or platinum-iridium alloys, etc.

Figure 4:
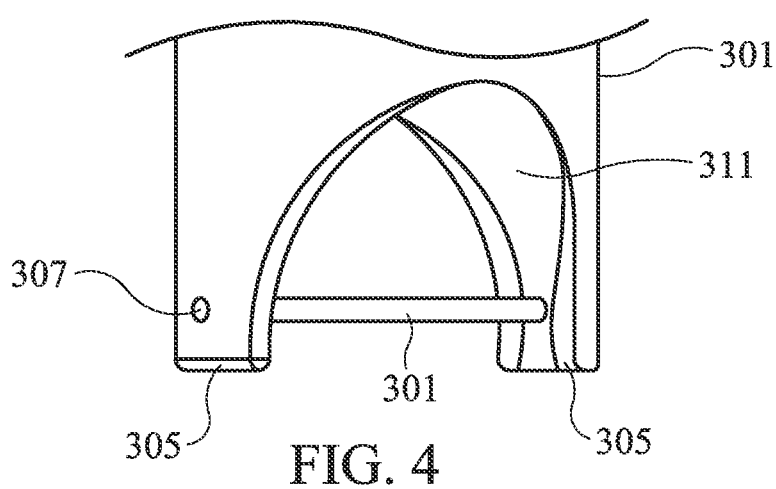
FIG. 4 is an enlarged, perspective view of a component of the system shown in FIG. 1.

FIG. 4 is an enlarged perspective view of catheter tip 103. Body 303 includes at least one second (non-cutting) area 311 having an arcuate shape which is opposite from and recessed with respect to the straight cutting wire 301. It is envisioned that body 303 and/or area 311 may be variously configured and dimensioned, such as, for example, planar, linear, arcuate, concave, convex, polygonal, irregular, uniform, non-uniform, staggered, tapered, consistent or variable, depending on the requirements of a particular application.

Figure 5:
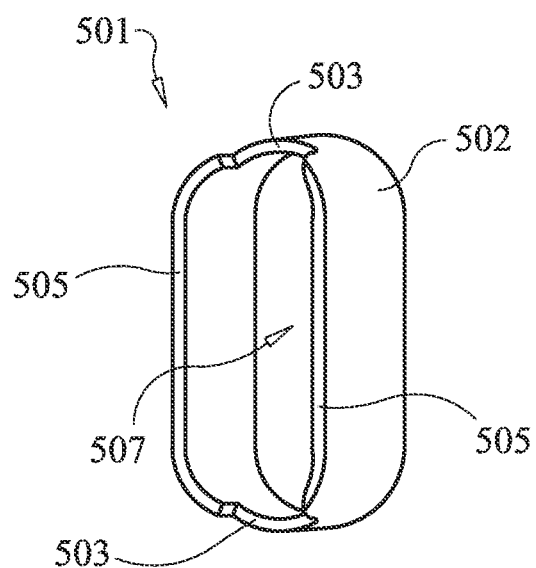
FIG. 5 is an enlarged, perspective view of a component of a catheter system in accordance with the principles of the present disclosure.

Further configurations of catheter tips are provided. For example, FIG. 5 is an enlarged perspective view of a catheter tip 501. Catheter tip 501 comprises a hollow oblong housing 502 having a recess 507. Housing 502 may be configured to be attached to a distal end of the shaft 101 having an oblong flattened shape such as that which is shown in FIG. 7. It is envisioned that all or only a portion of housing 502 may be variously configured and dimensioned, such as, for example, circular, oval, oblong, triangular, square, rectangular, polygonal, or irregular, depending on the requirements of a particular application.

Catheter tip 501 includes at least two opposing raised non-cutting areas 505 which are positioned along the elongated (i.e., longer) sides of housing 502. Catheter tip 501 includes at least two opposing recessed cutting edges 503 which are situated on the shorter ends of the housing 502 and which adjoin the raised non-cutting areas 505. In various embodiments, the non-cutting edges 505 protrude beyond the cutting edges 503.

Figure 6:
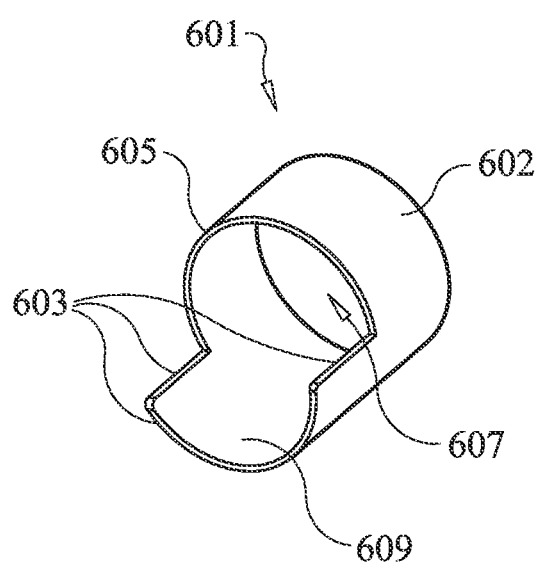
FIG. 6 is an enlarged, perspective view of a component of a catheter system in accordance with the principles of the present disclosure.

FIG. 6 is an enlarged perspective view of a catheter tip 601. Catheter tip 601 comprises a hollow cylindrical body 602 defining a cavity 607. A distal end of body 602 includes a protruding tip 609 shaped as a half-circle which extends from a portion of body 602. Tip 609 includes a plurality of cutting edges 603 which protrude from body 602. For example, cutting edges 603 may comprise one U-shaped edge which connects two straight edges that extend from body 602 in an axial direction. The body 602 includes a non-cutting edge 605 which is recessed from the cutting edges 603. The non-cutting edge 605 may comprise, e.g., a U-shaped edge. It is envisioned that all or only a portion of body 602, tip 609 and/or edges 603 may be variously configured and dimensioned, such as, for example, circular, oval, oblong, triangular, square, rectangular, polygonal, or irregular, depending on the requirements of a particular application.

Any alternate configurations of catheter tips may be contemplated which include cutting areas and non-cutting areas oriented in various planes, positions and locations on the catheter tip, and having various shapes and sizes.

FIG. 7 is an enlarged perspective view of catheter tip 501 attached to a distal end 707 of shaft 101. In various embodiments, shaft 101 may include one or more apertures of any desired shape or size to provide additional operational features. For example, shaft 101 may include an aperture 701 for irrigation capability, an aperture 703 for power, and an aperture 705 for suction capability. Additional features or apertures may be provided in shaft 101 which are capable of optionally passing materials such as guide wires, control wires, drugs, sensors, sensor fibers or wires, power, suction tubes, irrigation tubes, ultrasonic signals, drive shafts, etc.

Figure 8:
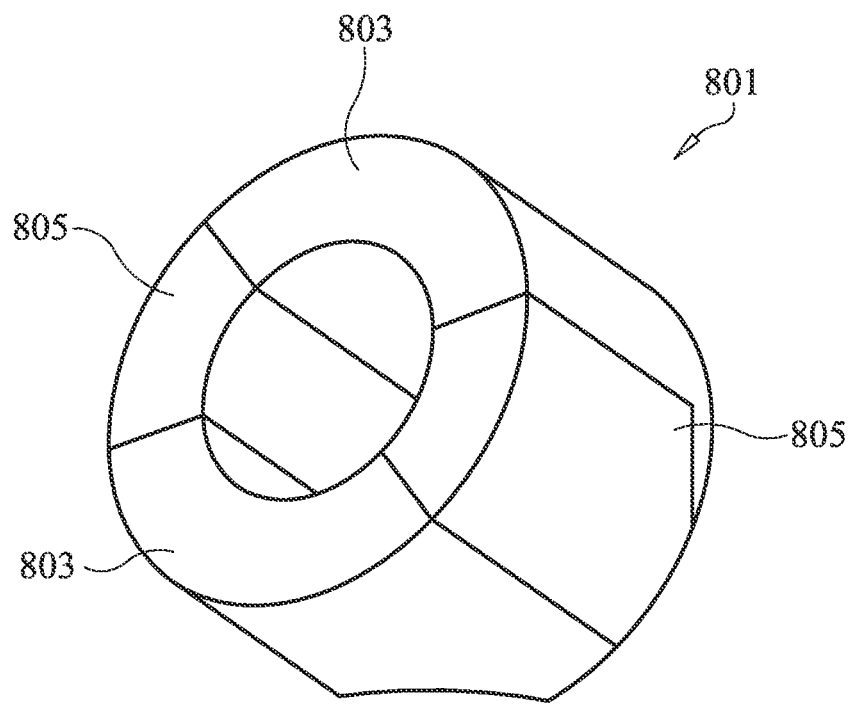
FIG. 8 is a perspective view of components of the system shown in FIG. 5.

In some embodiments, shaft 101 may be co-extruded with at least two different types of materials having different properties (different densities, hardness, flexibility, etc.). FIG. 8 is a perspective view of a co-extrusion shaft 801 in accordance with the principles of the present disclosure. Shaft 801 comprises a hollow cylindrical tube comprised of different materials, for example at least two different materials. In some embodiments, shaft 801 comprises at least two different materials which are co-extruded in a staggered configuration. For example, a first material 803 may be provided on opposing sides of shaft 801 which each adjoin a second material 805 also on opposing sides of shaft 801, as shown in FIG. 8. It is envisioned that the different characteristics and/or properties of the co-extruded materials 803, 805 may impart a desired range of motion, resiliency, flexibility, etc. to shaft 801. For example, shaft 801, while provided in a shape having a round cross-section, may be caused to deflect in a single plane (or any other predetermined direction) due to the selected hardness properties of each of the first and second materials 803, 805.

Figure 9:
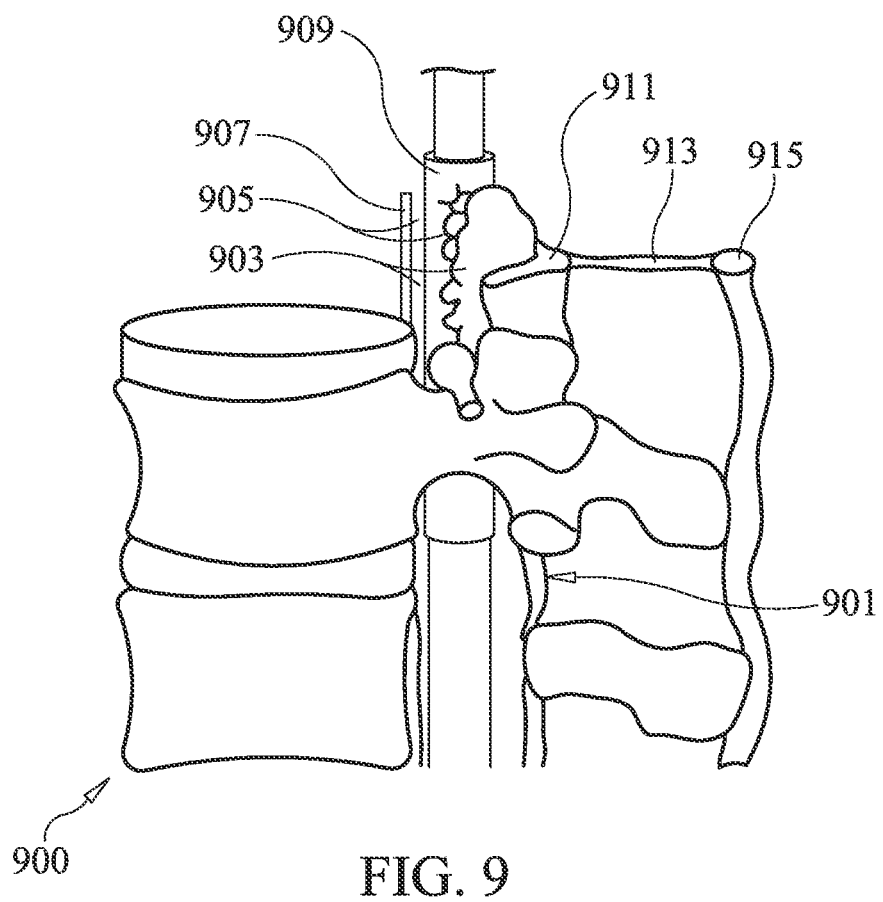
FIG. 9 is a plan view of a spinal segment of a human patient.

FIG. 9 is a plan view of an exemplary spinal segment 900 showing the orientation of various ligaments, tissues and voids, such as an interspinous space 901 (which can provide an access point for the catheter device), a ligamentum flavum 911, an interspinous ligament 913, a supraspinous ligament 915, spinal dura 909, a posterior longitudinal ligament 907, a venous plexus 905, and epidural fat 903. In some embodiments, the components of system 100 may be shaped or formed to fit in the interspinous space.

The components of system 100 may be sterilizable. In various embodiments, one or more components of system 100 are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In some embodiments, gamma radiation is used in the terminal sterilization step, which involves utilizing ionizing energy from gamma rays that penetrates deeply in the device and/or covering. Gamma rays are highly effective in killing microorganisms. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of system 100. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the catheter device and/or system is included in a gel. Other methods may also be used to sterilize one or more components of system 100 including gas sterilization, such as, for example, with ethylene oxide or steam sterilization.

In various embodiments, the catheter tip can be equipped with a camera for viewing tissue as the catheter is used in situ. The camera can be interconnected with a low power radio frequency transmitter so as to transmit images recorded by the camera to a display module in the operating room. Transmitters of this type are commercially available and can be adapted for the intended use. The image captured by the camera can be digitized and recorded by a camera. The image recorded by the camera can also be displayed real time on a video monitor through the wireless interconnection. The ease of a wireless transmission system in the confines of an operatory avoids the likelihood of a patient and attending health care providers from becoming entangled with cords and wires. In one embodiment, the camera can be located at the distal end of the catheter tip and a light source is provided so as to provide better images transmitted from the camera. In one embodiment the light source comprises at least one diode strategically placed on the catheter in order to provide amble but focused light on the area to be imaged by the camera.

A method for treating a surgical site is provided in accordance with the present disclosure which includes providing a catheter comprising a shaft shaped to fit into a desired surgical site, e.g., between two adjacent spinous processes. System 100 may be used in any suitable application. In some embodiments, system 100 may be used in treatment of lumbar spinal stenosis, vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing around trauma, contouring (cosmetic/plastic/reconstructive surgery), and others. System 100 may be used in a minimally invasive procedure via placement through a small incision, via delivery through a tube, cannula or other access device. The size and shape may be designed with restrictions on delivery conditions.

In assembly, operation and use, system 100 is employed with a surgical procedure, such as, for a treatment of a hypertrophied ligamentum flavum. It is contemplated that one or all of the components of system 100 can be delivered or implanted as a pre-assembled device or can be assembled in situ. System 100 may be completely or partially revised, removed or replaced.

In use, to treat a hypertrophied ligamentum flavum, the medical practitioner obtains access to a surgical site including in any appropriate manner, such as through the skin, or through an incision and retraction of tissues. In one embodiment, a drill is employed to remove bone tissue to provide access to a repair site. It is envisioned that system 100 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 100 is determined according to the configuration, dimension and location of a selected section of nerves and the requirements of a particular application.

An incision is made in the body of a patient and a cutting instrument (not shown) creates a surgical pathway for implantation of components of system 100. Shaft 101 is inserted into a surgical site 900 and is manipulated and steered such that tip 103 is deployed to a position adjacent ligamentum flavum 911. Cutting wire 301 is activated to dissect tissue as shaft 101 moves along ligamentum flavum 911. Ends 305 are shaped to protect adjacent tissue from being damaged during cutting. An irrigation or vacuum to supply suction can be attached to system 100 such that cut tissue can be removed from passageway 114 within shaft 101. In some embodiments, the shaft is flexible in at least a single plane to facilitate manipulation and positioning of the catheter device within the surgical site. In other applications, the catheter system may be applied to transverse processes or spinous processes of vertebrae.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

Although the invention has been described with reference to preferred embodiments, persons skilled in the art will recognize that changes may be made in form and detail without departing from the spirit and scope of the invention.

What is claimed is:

1. A catheter system for operating on tissue at a surgical site in a patient, the catheter system comprising:
    an elongated shaft defining an axis, the shaft having a proximal end, a distal end, and an outer surface, the outer surface defining a circumference, and including at least one slot-like, non-circumferential cavity extending through at least a portion of the outer surface substantially perpendicular to the axis, the at least one cavity being configured to define a bending movement of the distal end relative to the proximal end; and
    a catheter tip attached to the distal end of the shaft, the catheter tip comprising a curved body having at least one cutting edge, and at least one non-cutting area recessed from the at least one cutting edge;
    wherein the bending movement of the distal end relative to the proximal end defined by the at least one cavity is adapted to facilitate deflection and steering of the shaft through the patient to the surgical site.

2. The catheter system of claim 1, wherein the shaft is deflectable in a single plane.

3. The catheter system of claim 1, wherein the at least one cutting edge comprises at least one RF cutting edge, the at least one RF cutting edge including at least one electrode configured to emit a cutting radio frequency signal and the at least one non-cutting area, the at least one non-cutting area being insulated, thereby substantially localizing the radio frequency signal at the at least one RF cutting edge.

4. The catheter system of claim 3, further comprising a radio frequency generator operably connected to the catheter tip to provide radio frequency energy to the at least one electrode.

5. The catheter system of claim 1, wherein the at least one cutting edge comprises a cutting wire attached to two opposing tips extending from the curved body.

6. The catheter system of claim 3, wherein the catheter tip comprises a hollow oblong housing having a recess, said at least one non-cutting area comprises at least two opposing raised non-cutting edges having a first height, and said at least one RF edge comprises at least two opposing recessed cutting edges having a second height.

7. The catheter system of claim 1, further comprising a camera configured for imaging the tissue.

8. The catheter system of claim 6, wherein the first height is greater than the second height.

9. The catheter system of claim 1, wherein the catheter tip comprises a hollow substantially cylindrical body having a cavity and including a protruding tip shaped as a substantial half-circle which extends from a portion of the substantially cylindrical body, the protruding tip including the at least one cutting edge, the at least one cutting edge comprising a plurality of cutting edges, wherein the body includes the at least one non-cutting area, the at least one non-cutting area being recessed from the plurality of cutting edges.

10. The catheter system of claim 9, wherein the plurality of cutting edges define a substantially U-shaped cutting edge which connects two straight edges that extend from the substantially hollow cylindrical body in the axial direction, an upper-open portion of the substantially U-shaped cutting edge being oriented toward the distal end of the shaft.

11. The catheter system of claim 9, wherein the recessed non-cutting area comprises a substantially U-shaped non-cutting edge, an upper-open portion of the substantially U-shaped cutting edge being oriented toward the distal end of the shaft.

12. The catheter system of claim 1, wherein the shaft is comprised of at least two co-extruded materials, each of the at least two co-extruded materials having different material properties.

13. A steerable catheter system for operating on tissue at a surgical site in a patient, the steerable catheter system comprising:
    an elongated shaft defining an axis, the shaft having a proximal end, a distal end, an inner surface, the inner surface defining a passageway, and an outer surface, the outer surface defining a circumference and including at least one slot-like non-circumferential cavity extending through at least a portion of the outer surface substantially perpendicular to the axis, the at least one cavity being configured to define a bending movement of the distal end relative to the proximal end;
a catheter tip attached to the distal end of the shaft, wherein the catheter tip comprises a curved body having at least one radio frequency (RF) cutting edge and at least one non-cutting area recessed from the at least one RF cutting edge;
at least one electrode disposed on the at least one RF cutting edge and configured to emit a cutting radio frequency signal;
a radio frequency generator operably connected to the catheter tip to provide radio frequency energy to the at least one electrode; and
a vacuum configured for attachment to the proximal end of the shaft so as to provide suction to clear cut tissue from the passageway;
wherein the bending movement of the distal end relative to the proximal end defined by the at least one cavity is adapted to facilitate deflection and steering of the shaft through the patient to the surgical site.

14. The catheter system of claim 13, wherein the at least one non-cutting area is arcuate and recessed from the at least one RF cutting edge.

15. The catheter system of claim 13, wherein the catheter tip comprises a hollow oblong housing having a recess, said housing including the at least one non-cutting area and the at least one RF cutting edge, the at least one non-cutting edge comprising at least two opposing raised non-cutting areas and the at least one RF cutting edge comprising at least two opposing recessed cutting edges, wherein the at least two raised non-cutting areas are positioned on opposing sides of the oblong housing having a first height, and wherein the at least two recessed cutting edges are positioned on opposing sides of the oblong housing having a second height, the first height being greater than the second height, the at least two raised non-cutting areas being located.

16. The catheter system of claim 13, wherein the catheter tip comprises a hollow substantially cylindrical body having a cavity and including a protruding tip shaped as a substantial half-circle which extends from a portion of the substantially cylindrical body, the protruding tip including the at least one RF cutting edge, the at least one RF cutting edge comprising a plurality of cutting edges, wherein the body includes the at least one non-cutting area, the at least one non-cutting area being recessed from the cutting edges.

17. The catheter system of claim 13, further comprising a camera configured for imaging tissue.

18. A method of treating a hypertrophied ligamentum flavum at a surgical site in a patient, the method comprising:
utilizing a catheter system, the catheter system comprising:
an elongated shaft defining an axis, the shaft having a proximal end, a distal end, an inner surface the inner surface defining a passageway, and an outer surface, the outer surface defining a circumference and including at least one slot-like non-circumferential cavity extending through at least a portion of the outer surface substantially perpendicular to the axis, the at least one cavity being configured to define a bending movement of the distal end relative to the proximal end,
a catheter tip attached to the distal end of the shaft, wherein the catheter tip comprises a curved body having at least one radio frequency (RF) cutting edge and at least one non-cutting area recessed from the at least one cutting edge,
at least one electrode disposed on the at least one RF cutting edge and configured to emit a cutting radio frequency signal,
a radio frequency generator operably connected to the catheter tip to provide radio frequency energy to the at least one electrode, and
a vacuum attached to the proximal end of the shaft so as to provide suction to clear cut tissue from the passageway,
wherein the bending movement of the distal end relative to the proximal end defined by the at least one cavity is adapted to facilitate deflection and steering of the shaft through the patient to the surgical site,
utilizing the bending movement defined by the at least one cavity on the outer surface of the shaft to steer the shaft through the patient;
positioning the catheter tip adjacent the hypertrophied ligamentum flavum;
activating the radio frequency generator; and
cutting tissue from the hypertrophied ligamentum flavum with the at least one RF cutting edge.

19. The method of claim 18, wherein the catheter tip comprises a hollow oblong housing having a recess, said housing including the at least one non-cutting area and the at least one RF cutting edge, the at least one non-cutting area comprising at least two opposing raised non-cutting edges having a first height, and the at least one RF cutting edge comprising at least two opposing recessed cutting edges, the at least two recessed cutting edges being positioned on opposing sides of the oblong housing having a second height, the first height being greater than the second height.

20. The method of claim 18, wherein the catheter tip comprises a hollow substantially cylindrical body having a cavity and including a protruding tip shaped as a substantial half-circle which extends from a portion of the substantially cylindrical body, the protruding tip including the at least one cutting edge, the at least one cutting edge comprising a plurality of cutting edges, wherein the body includes the non-cutting area which is recessed from the cutting edges.

21. The catheter system of claim 1, wherein the at least one slot-like non-circumferential cavity comprises a plurality of slot-like non-circumferential cavities defined at spaced intervals on the outer surface, each of the plurality of slot-like non-circumferential cavities being substantially perpendicular to the axis.

22. The catheter system of claim 21, wherein the spaced intervals of a first plurality of the plurality of recesses proximate the distal end of the elongated shaft are less than the spaced intervals of a second plurality of the spaced intervals proximate the proximal end of the elongated shaft.

* * * * *

UNITED STATES PATENT AND TRADEMARK OFFICE
CERTIFICATE OF CORRECTION

PATENT NO.         : 9,216,057 B2                                    Page 1 of 1
APPLICATION NO.    : 13/840010
DATED              : December 22, 2015
INVENTOR(S)        : Goshayeshgar et al.

It is certified that error appears in the above-identified patent and that said Letters Patent is hereby corrected as shown below:

Title page,

Item (71), under "Applicant", in Column 1, Line 1, delete "Kyphon SARL, Neuchatel (CH)" and insert -- Kyphon SÀRL, Neuchâtel (CH) --, therefor.

Item (73), under "Assignee", in Column 1, Line 1, delete "Kyphon SARL, Neuchatel (CH)" and insert -- Kyphon SÀRL, Neuchâtel (CH) --, therefor.

Specification,

In Column 1, Line 17, delete "(LSS)," and insert -- (LSS). --, therefor.

In Column 1, Line 46, delete "challengers" and insert -- challenges --, therefor.

Claims,

In Column 13, Line 53, in Claim 18, delete "surface" and insert -- surface, --, therefor.

Signed and Sealed this
Seventeenth Day of May, 2016

Michelle K. Lee
*Director of the United States Patent and Trademark Office*